(12) United States Patent
Hochrainer

(10) Patent No.: US 9,027,547 B2
(45) Date of Patent: May 12, 2015

(54) DRIVE UNIT FOR DOSAGE COUNTER

(75) Inventor: Dieter Hochrainer, Schmallenberg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 878 days.

(21) Appl. No.: 13/059,724

(22) PCT Filed: Aug. 26, 2009

(86) PCT No.: PCT/EP2009/061023
§ 371 (c)(1),
(2), (4) Date: Apr. 8, 2011

(87) PCT Pub. No.: WO2010/023233
PCT Pub. Date: Mar. 4, 2010

(65) Prior Publication Data
US 2011/0259324 A1    Oct. 27, 2011

(30) Foreign Application Priority Data
Aug. 28, 2008    (DE) .......................... 10 2008 044 770

(51) Int. Cl.
*A61M 11/00*    (2006.01)
*A61M 15/00*    (2006.01)

(52) U.S. Cl.
CPC ......... *A61M 15/009* (2013.01); *A61M 15/0073* (2014.02)

(58) Field of Classification Search
CPC .............. A61M 2015/0068; A61M 2015/007; A61M 2015/0071; A61M 2015/0073; A61M 2015/0075; A61M 2015/0078; A61M 15/0073; A61M 15/009
USPC ............ 128/200.14, 200.23, 203.12, 203.23, 128/203.24; 222/43, 38, 37, 36, 14, 16, 222/401, 402.1, 402.11, 410
See application file for complete search history.

(56) References Cited

U.S. PATENT DOCUMENTS

| 5,988,496 A * | 11/1999 | Bruna ........................ 235/91 R |
| 6,164,494 A * | 12/2000 | Marelli ........................... 222/38 |
| 6,283,365 B1 * | 9/2001 | Bason ........................... 235/116 |
| 6,431,168 B1 * | 8/2002 | Rand et al. ............... 128/200.23 |
| 6,997,349 B2 * | 2/2006 | Blacker et al. ................... 222/23 |
| 7,004,164 B2 * | 2/2006 | Scarrott ................... 128/205.23 |
| 7,100,530 B2 * | 9/2006 | Lu ................................. 116/307 |
| 7,156,258 B2 * | 1/2007 | Eckert .............................. 222/23 |

(Continued)

FOREIGN PATENT DOCUMENTS

| CA | 2464292 A1 | 12/2003 |
| CA | 2587612 A1 | 5/2006 |

(Continued)

OTHER PUBLICATIONS

International Search Report, Form PCT/ISA/210, for corresponding PCT/EP2009/061023; date of mailing: Nov. 18, 2009.

*Primary Examiner* — Rachel Young
*Assistant Examiner* — LaToya M Louis
(74) *Attorney, Agent, or Firm* — Michael P. Morris; Mary-Ellen M. Devlin

(57) ABSTRACT

A nebulizer which is a metered dose inhaler for use in administering medicaments with an associated does counter, which can, by way of a guide track or inclined plane and an associated guide element, cause an axial movement occurring on actuation of the nebulizer to be partly converted into a rotary movement for driving a counting ring, which can count both complete and incomplete actuations.

16 Claims, 4 Drawing Sheets

(56) References Cited

U.S. PATENT DOCUMENTS

| | | |
|---|---|---|
| 7,341,057 B2* | 3/2008 | Scarrott et al. ............ 128/200.23 |
| 7,510,100 B2* | 3/2009 | Stradella et al. ................. 222/36 |
| 7,726,588 B2* | 6/2010 | Wuttke et al. .................. 239/321 |
| 7,780,038 B2* | 8/2010 | Ingram et al. .................... 222/36 |
| 8,740,014 B2* | 6/2014 | Purkins et al. ................... 222/36 |
| 2004/0144798 A1* | 7/2004 | Ouyang et al. ................... 222/36 |
| 2004/0149772 A1* | 8/2004 | Ouyang ............................ 222/36 |
| 2004/0211420 A1* | 10/2004 | Minshull et al. ......... 128/203.15 |
| 2007/0235027 A1* | 10/2007 | Schuckmann ........... 128/200.17 |
| 2008/0105702 A1* | 5/2008 | Mochizuki et al. ............. 222/36 |
| 2009/0101150 A1* | 4/2009 | Stradella et al. ......... 128/205.23 |

FOREIGN PATENT DOCUMENTS

| | | |
|---|---|---|
| DE | 102006049614 A1 | 4/2008 |
| WO | 03107269 A1 | 12/2003 |
| WO | 2006051073 A1 | 5/2006 |

* cited by examiner

DRIVE UNIT FOR DOSAGE COUNTER

BACKGROUND OF THE INVENTION

1. Field of the Invention

The present invention relates to a nebulizer for dispensing medicament with associated means for counting doses administered by the nebulizer.

The present invention preferably relates to nebulisers in the form of inhalers. In particular, the invention relates to so-called Metered Dose Inhalers (MDIs), i.e. inhalers in which a liquid medicament formulation is dispensed as an aerosol, or nebulised, from a pressurised container (aerosol container) by means of a metering valve, in particular. However, the present invention can also be used for other inhalers or nebulisers in which it is important to count the number of doses dispensed.

2. Description of Related Art

WO 00/09187 A1, which constitutes the starting point, discloses an MDI with a counting device for counting actuations and/or aerosol doses dispensed. On actuation, a container that holds the medicament formulation to be dispensed is pressed into a housing of the MDI. This stroke movement is detected by the counting device and drives a counting ring. For this purpose, the counting device has an elastically deformable drive element resembling a bell-crank lever. When the MDI is actuated, the drive element is moved both axially and in the direction of rotation (circumferential direction) of the counting ring at the same time, so as to rotate the counting ring further.

The elastic deformation of the drive element in the known MDI may be problematic. In particular, satisfactory resetting of the drive element is absolutely necessary if problem-free operation of the counting device is to be guaranteed. This requires very narrow manufacturing tolerances.

A further problem or disadvantage of the known MDI is the fact that incomplete actuation—i.e. where the container is only partly moved—does not ensure that the counting device or counting ring is reliably moved on, even when a dose is dispensed in spite of only partial actuation.

A BRIEF SUMMARY OF THE INVENTION

The problem of the present invention is to provide a nebuliser having an improved counting device.

The above problem is solved with a nebulizer according to the present invention as described herein.

In one aspect of the present invention, the drive device of the counter comprises a first guide track and/or an inclined plane and an associated guide element for converting an axial movement into a rotary movement for driving the counting ring or an associated gearwheel. This allows positive driving or rotating and counting, with elastic deformation of the drive element neither needed nor provided. This allows a construction which is particularly reliable in operation, while avoiding elastic deformation of the drive element.

In a second aspect of the present invention which can also be implemented independently, the drive element is annular with axial teeth and/or of rigid construction. This again provides a simple construction which is reliable in operation.

In a third aspect of the present invention which can also be implemented independently, the nebuliser or counter is configured such that even a partial actuation of the nebuliser is sufficient to move the counter on. This leads to particularly reliable counting and hence very reliable operation of the nebuliser.

BRIEF DESCRIPTION OF THE SEVERAL VIEWS OF THE DRAWINGS

Further advantages, features, properties and aspects of the present invention will become apparent from the following description of a preferred embodiment, by reference to the drawings, wherein.

DETAILED DESCRIPTION OF THE INVENTION

Figure 1:
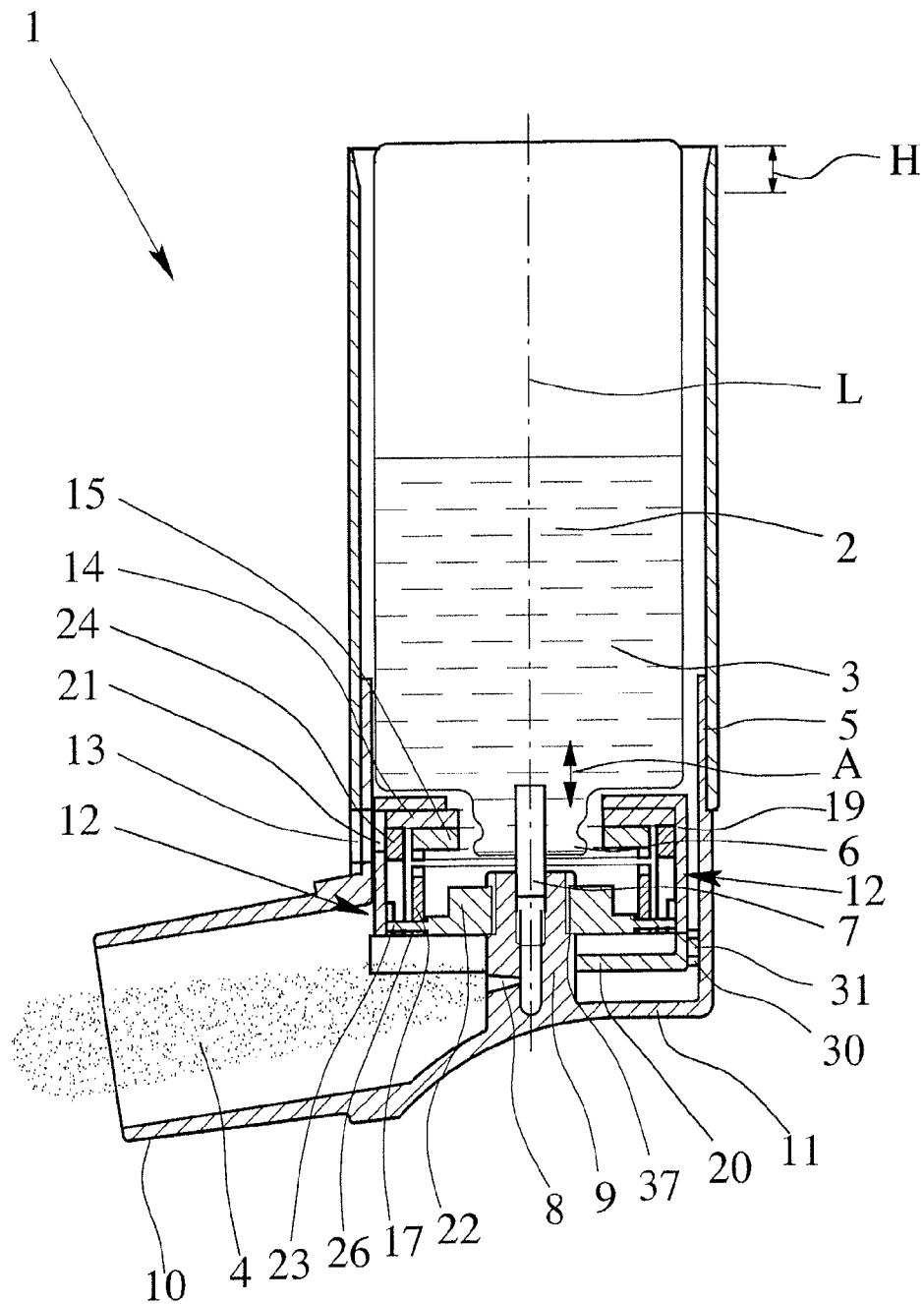
FIG. 1 is a schematic section through a proposed nebuliser with a counter.

In the Figures, the same reference numerals are used for identical or similar parts, while corresponding or comparable properties and advantages are achieved even when the description is not repeated.

FIG. 1 shows, in a purely schematic section, a preferred embodiment of a nebuliser 1 according to the present invention. The nebuliser 1 is, in particular, an inhaler, preferably an MDI.

In particular, the nebuliser 1 is designed to deliver a medicament formulation or a fluid 2 from a container 3 as a spray mist or aerosol 4, as shown schematically in FIG. 1. It should be noted that FIG. 1 shows the nebuliser 1 in the unactuated state, but the spray mist or aerosol 4 is shown for illustration purposes.

In the embodiment shown the nebuliser 1 has a housing 5 into which the container 3 preferably has been inserted or can be inserted. However, other design solutions are also possible.

The nebuliser 1 or container 3 preferably comprises a valve 6, particularly a metering valve. Particularly preferably, the valve 6 comprises a valve element that can be moved in particular to open the valve 6, particularly a valve stem 7 that can be pressed in axially. However, other design solutions are possible here, too.

The nebuliser 1 preferably comprises a spray device or nozzle 8 which is attached to the container 3 or to the valve 6 or its valve element or valve stem 7—via a connecting member 9 in the embodiment shown—for dispensing the fluid 2 by spraying or for forming the aerosol 4 on actuation of the nebuliser 1. Preferably, the nozzle 8 is formed by the connecting member 9, particularly in a side surface of the preferably substantially hollow cylindrical connecting member 9. However, other design solutions are possible here too.

The nebuliser 1 preferably comprises a mouthpiece 10 or other endpiece for delivering the aerosol 4, which is particularly preferably formed or held by a housing part 11 in the form of an angle member. However, other design solutions are possible here too.

The nebuliser 1 or its housing 5 and/or container 3 is or are preferably of elongate construction. The aerosol 4 is preferably dispensed diagonally or at right-angles to this longitudinal direction L. The mouthpiece 10 or other endpiece is preferably correspondingly angled or adapted to be folded away, optionally also adjustable, particularly pivotable.

On actuation of the nebuliser 1 the valve 6 is opened and in particular only one dose of the fluid 2 is delivered through the valve stem 7, the connecting member 9 and the nozzle 8. In the nozzle 8 the medicament is atomised or nebulised as an aerosol 4 which is dispensed through the mouthpiece 10 or other endpiece. The aerosol 4 can then be inhaled.

The actuation of the nebuliser or the opening of the valve is preferably carried out by axially pressing in the valve stem 7 or otherwise actuating the valve 6.

In the embodiment shown, during the actuation of the nebuliser 1, or for the purpose of actuating it, the container 3 or the valve 6 is or are moved or compressed on the one hand relative to the connecting member 9 or housing part 11 or on the other hand relative to one another, particularly in the direction of the longitudinal axis L, in an axial movement as indicated by the arrow A. In the embodiment shown, this is done by manually pressing the container 3 by its base (at the top in FIG. 1) further into the open housing 5—in particular counter to the spring force of the valve 6 and/or another spring element. However, the actuation may also be carried out in reverse manner by pressing onto the housing part 11 (angle member) or another actuating part, in which case the housing 5 is then closed off at the top, for example, and the housing part 11 or other part can be slid along, actuated or pressed in relative to the housing 5.

However, other design solutions are also possible for actuating the nebuliser 1.

The axial movement A opens the valve 6, and a dose of the fluid 2 is dispensed. When the nebuliser 1 is actuated fully, i.e. when there is a complete axial movement A, the container 3 or other actuating member of the nebuliser—such as the housing part 11, the connecting member 9, the valve element, such as the valve stem 7, or the like—executes a stroke H, particularly relative to the valve 6 or housing 5.

Depending on the construction of the nebuliser 1 or valve 6, the aerosol 4 is often delivered, i.e. a dose of the fluid 2 is dispensed, even when the stroke H is incomplete—i.e. when actuation is incomplete.

The nebuliser 1 has a counter 12 for counting actuations of the nebuliser 1 or of doses of aerosol dispensed. The counter 12 is schematically shown in section in FIG. 1. It is preferably disposed in or on the housing 5, particularly the head piece, angle member or housing part 11, and/or on the top of the container 3. However, other design solutions are possible here too.

The totals counted by the counter 12 can be indicated or read off through a viewing window 13, which is formed in the housing 5 and/or in the housing part 11 here.

The counter 12 may for example indicate the number of aerosol doses still available or the number of actuations that have already taken place or the number of aerosol doses dispensed, as the numerical value displayed.

The counter 12 preferably comprises at least one counting ring 14 and/or an associated gearwheel 15.

According to an alternative embodiment, the gearwheel 15 may also form a first counting ring and the counting ring 14 may form a second counting ring. In particular the gearwheel 15 is preferably then coupled to the counting ring 14 via a stepping-down gear (not shown) so that after a certain number of counting steps of the gearwheel 15 the counting ring 14 is then advanced or further rotated by one counting step.

If only one counting ring 14 or one additional counting ring is also provided, the gearwheel 15 can be selectively coupled to the counting ring 14 directly or via a stepping down gear or if necessary may even be formed directly by the counting ring 14 or integrally formed therewith.

The alternative features mentioned above are particularly preferably also covered by the description or phrase "the gearwheel 15 is associated with the counting ring 14".

Figure 2:
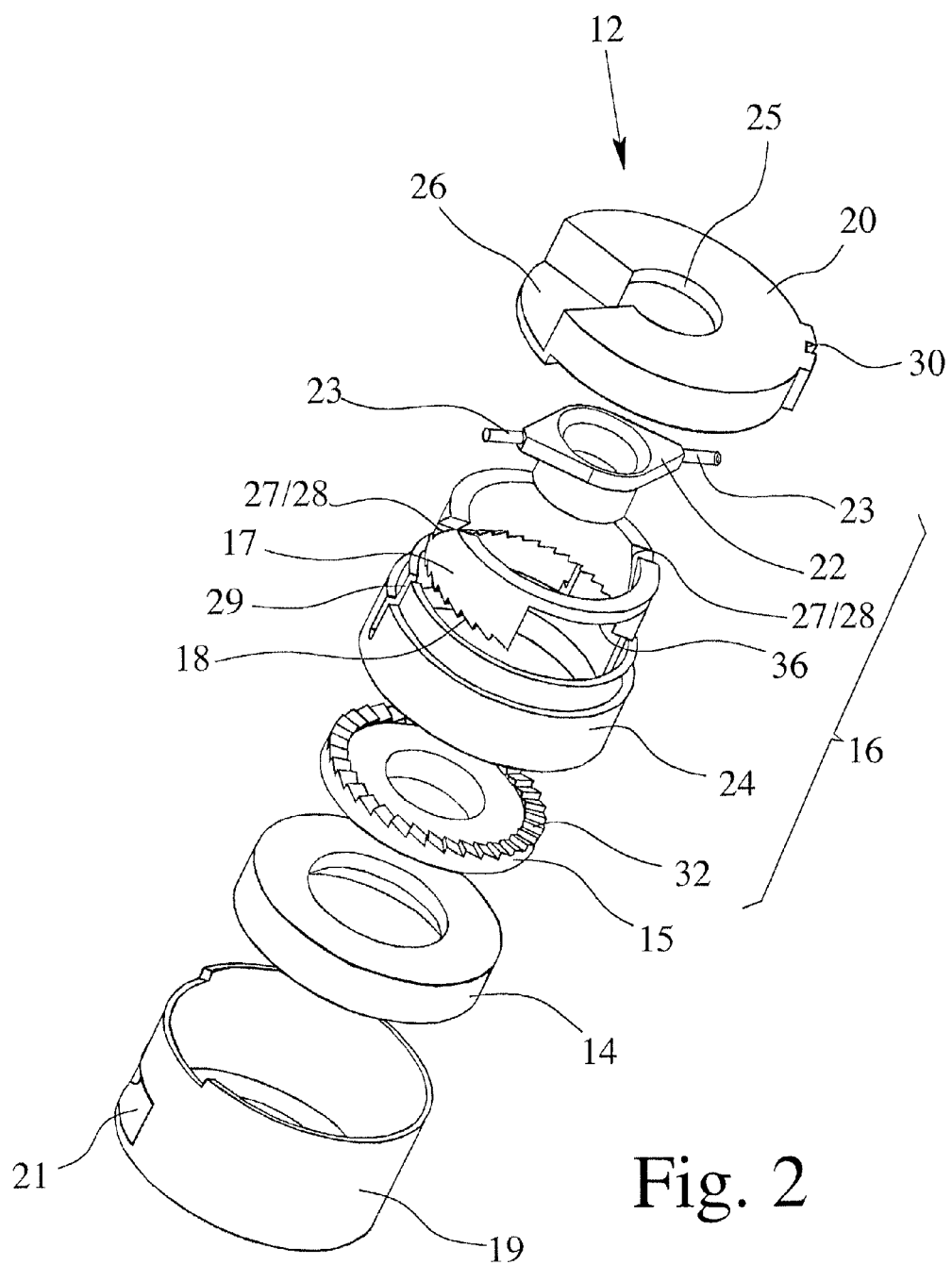
FIG. 2 is an exploded view of parts of the counter.

The counter 12 further comprises a drive device 16 for driving the counting ring 14 or gearwheel 15, particularly by stepwise rotation, as shown in exploded view in FIG. 2.

The drive device 16 comprises a drive element 17 which is associated with the counting ring 14 or gearwheel 15 for stepwise further rotation.

Preferably, the drive element 17 is at least substantially annular, with axial teeth 18 and/or of rigid construction. The teeth 18 correspond to the teeth 32 on the gearwheel 15, although there is no need for teeth to be provided over the entire underside of the drive element 17 and/or over the entire surface of the gearwheel 15. If desired only individual teeth may be provided.

In particular, the drive element 17 can be moved first of all towards the counting ring 14 or gearwheel 15 and particularly preferably can only be rotated jointly with them afterwards.

Preferably, the nebuliser 1 or counter 12 or the drive device 16 thereof is or are constructed such that even partial actuation of the nebuliser 1 or a partial stroke H is sufficient to move the counter 12 on or rotate the gearwheel 15 or counting ring 14 by one counting step. A possible design solution will become apparent from the more detailed description of a preferred construction of the counter 12 that follows.

Figure 3:
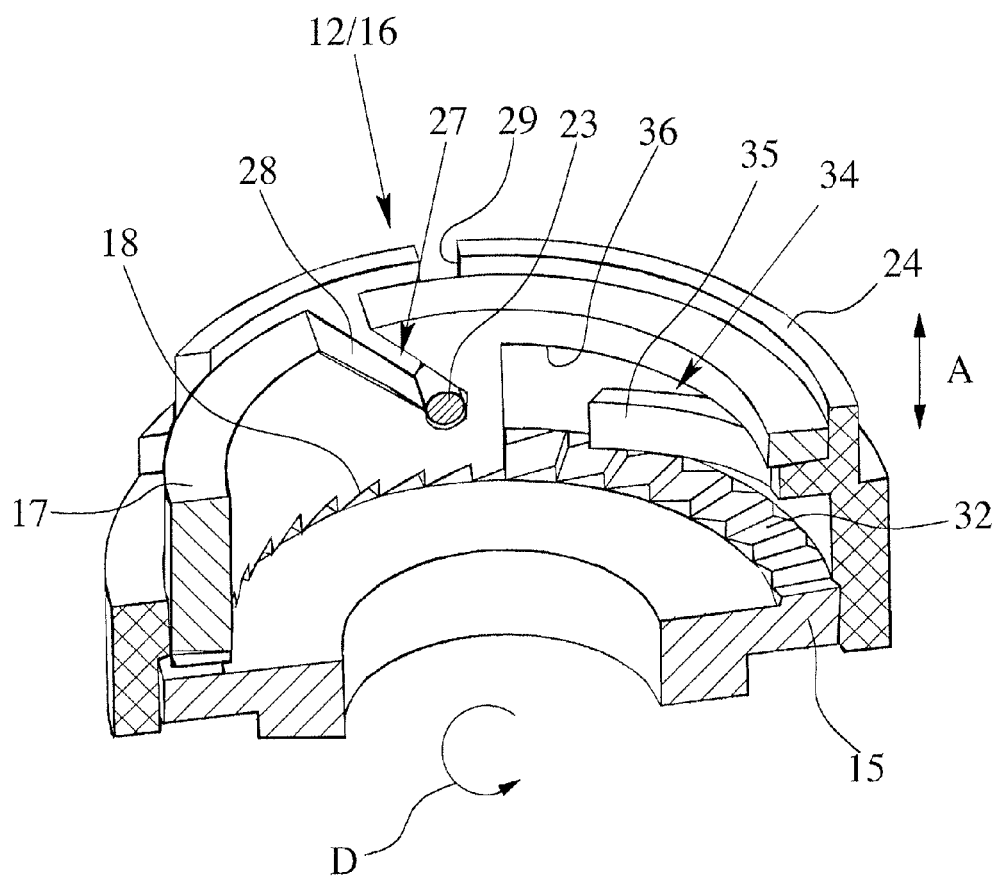
FIG. 3 is a schematic partial section through the counter without a housing, with the nebuliser actuated.
Figure 4:
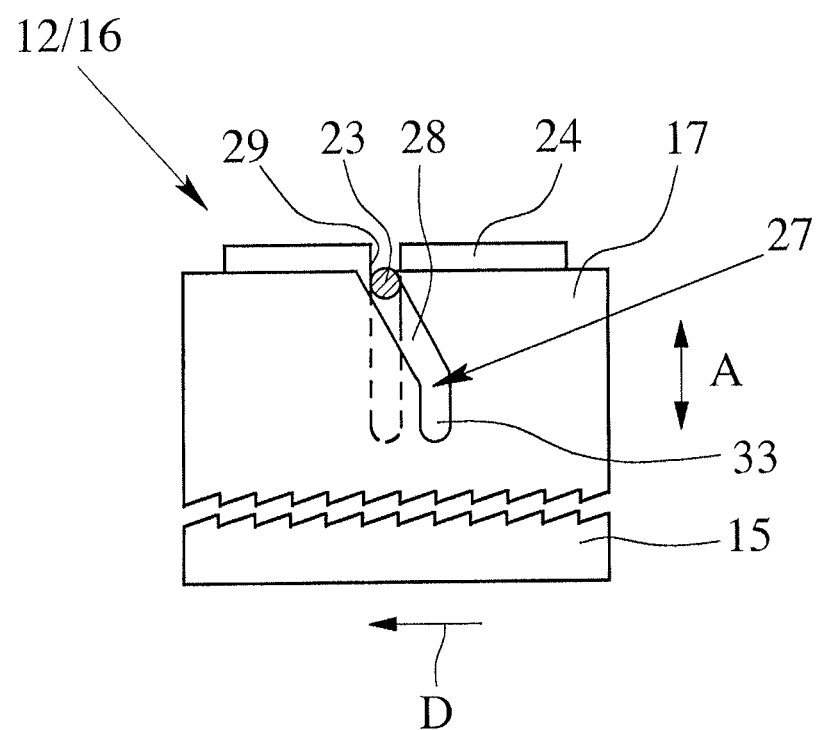
FIG. 4 is a schematic representation in the manner of a development of a drive device of the counter at the start of actuation of the nebuliser.

As an illustration of a preferred construction of the counter 12 and/or the preferred function of the counter 12, reference is hereinafter made to FIGS. 2 to 4 in addition to FIG. 1. FIG. 2 shows components or parts of the counter 12 in an exploded view. FIG. 3 shows, in schematic partial section, a part of the counter 12 with the nebuliser 1 actuated. FIG. 4 shows in a schematic development parts of the counter 12 or drive device 16 at an initial stage of the actuation of the nebuliser 1.

The counter 12 preferably comprises a counter housing which in this case is made up of a lower part 19 and an upper part 20. The terms "lower part" and "upper part" are used only for ease of description but do not provide any information as to their orientation when the nebuliser 1 or counter 12 is in used. In addition, other design solutions are also possible.

In the counter housing—in the lower part 19 in the embodiment shown—there is preferably a viewing window 21 for displaying or showing the numerical values of the counter 12 so that they can be read off. The viewing window 21 is associated with the window 13, in particular. For example, the viewing window 21 may be a gap or opening, particularly if the window 13 is transparent but is closed off by a wall. Conversely it is also possible for the viewing window to be closed off by a wall, cover or the like but still be transparent.

The counter 12 also preferably comprises a guide part 22 with at least one guide element 23, in particular two guide elements 23 arranged on opposite sides, and preferably a guide sleeve 24.

The counter device 12 is preferably fitted into the nebuliser 1 or the housing 5 or housing part 11 so as to abut on the container 3 or on a so-called valve plate of the container 3/valve 6—with the lower part 19 in the embodiment shown—and/or so as to accommodate or embrace the valve element, such as the valve stem 7. The connecting member 9 preferably extends through a central opening 25 in the upper part 20 into the counter housing as far as the valve 6 or valve stem 7. In particular, the connecting member 9 forms a valve stem receptacle and has for this purpose a central bore, recess or the like with a nozzle 8 preferably attached thereto.

On actuation of the nebuliser 1 the axial movement A causes the connecting member 9 to penetrate more deeply into the counter housing, in particular it causes the lower part 19 and upper part 20 to be moved along the longitudinal axis L—upwards, in the representation shown in FIG. 1—relative to the connecting member 9. The counter housing or upper part 20 preferably has a sector-like peripheral depression 26 in the embodiment shown which broadens radially outwards in the circumferential direction, to ensure that even when the nebuliser 1 is actuated when the connecting member 9 is located deeper in the upper part 20, the nozzle 8 can deliver the aerosol 4 in the desired manner, laterally in the direction of the mouthpiece 10 or other endpiece. However, other design solutions are possible here too.

The guide part 22 preferably fits onto the connecting member 9. Preferably, the connecting member 9 passes through the guide part 22. Particularly preferably, this guide part 22 is axially supported on the connecting member 9, so that during the axial movement A or during actuation of the nebuliser 1, the guide part 22 cannot be pushed further onto the connection member 9 in the axial direction. This can be ensured for example by a corresponding axial abutment, such as a shoulder 37 which is shown purely schematically in FIG. 1.

Instead of being supported on the connecting member 9 the guide part 22 may also be supported on a different part of the nebuliser 1, particularly the housing part 11.

The guide elements 23 preferably extend radially outwards from the guide part 22, particularly on opposite sides.

The guide elements 23 are preferably constructed in the manner of pegs.

Where reference is made hereinafter to only one guide element 23, this is because a single guide element 23 is theoretically sufficient to perform the function, even though preferably two guide elements 23 will be provided on opposite sides for reasons of design, stability and/or safety.

The counter 12 or drive device 16 preferably has a first guide track 27 and/or an inclined plane 28 for the guide element 23, or even, in the embodiment shown, two first guide tracks 27 or inclined planes 28 for the two guide elements 23.

The first guide track 27 or inclined plane 28 is preferably formed in or by the drive element 17. However, other design solutions are also possible.

The guide elements 23 each preferably pass radially through their associated first guide tracks 27 and are preferably each guided by their free ends in second guide tracks 29, which are preferably formed in or by the guide sleeve 24.

Preferably, the second guide tracks 29 run only in the axial direction. Accordingly, the guide elements 23 are each guided to be movable only in the axial direction relative to the rotation axis of the counting ring 14 or gearwheel 15. However, other design solutions are possible here as well.

Depending on the construction, the guide tracks 27 and/or 29 may selectively be formed as a slot, groove or the like.

The guide sleeve 24 is preferably installed in the counter housing so as to rotate therewith. The counter housing is in turn preferably installed in the nebuliser 1 so as to rotate therewith. For this purpose, the upper part 20 comprises, for example, an exterior axial groove 30 into which a radial and/or web-like projection 31 or a spring of the nebuliser 1 or housing 5 or housing part 11 engages, as shown in FIG. 1, to create a non-rotational but displaceable connection with the counter housing. However, other design solutions are possible here as well.

The gearwheel 15 is provided with preferably axial teeth 32 which take the form of saw teeth, in particular, and/or correspond to the teeth 18 of the drive element 17 such that in the axially contracted state the drive element 17 is able to drive or further rotate or co-rotate the gearwheel 15 at least or only in a direction of rotation D (the counting direction), as shown in FIG. 3.

Numbers or numerical values, not shown in the Figures, are preferably arranged on the peripheral circumferential surface or other suitable area of the counting ring 14 and/or gearwheel 15 and can be seen from outside through the windows 13, 21, so as to indicate the current total on the counter 12.

The guide track 27 or 29 or the inclined plane 28 preferably forms a slot or a groove in which the associated guide element 23 engages. However, other design solutions are also possible.

FIG. 4 illustrates the operating principle of the proposed drive device 16 of the counter 12.

The guide elements 23 are each guided so as to be movable only in the axial direction in the second guide track 29 relative to the rotation axis of the counting ring 14/gearwheel 15, i.e. the guide part 22 is secured against rotation. Alternatively or additionally, the guide part 22 may also be held directly on the housing part 11 or connecting member 9 and/or secured against rotation in some other way.

When the nebuliser 1 is not actuated, the drive element 17 is preferably axially spaced from the associated counting wheel 14 or gearwheel 15. When the nebuliser 1 is actuated the axial movement A of the guide elements towards the counting ring 14 or gearwheel 15 takes place. At the start of this axial movement, which is shown in FIG. 4, the drive element 17 is initially pushed axially towards the counting ring 14 or the gear wheel 15 so that the teeth 18 and 32 are brought into engagement with one another. This is achieved by the fact that the guide elements act on the drive element 17 via the first guide tracks 27, and in particular form a slide-like guide or positive guide. Preferably, the guide elements 23 cooperate with the sloping planes 28 such that at the start of the axial movement A initially the drive element 17 is axially moved only or substantially towards the gearwheel 15 until the teeth engage.

In the course of the further axial movement A of the guide elements 23 the drive element A is rotated in the direction of rotation D together with the gearwheel 15 that rotates with it as a result of the meshing of the teeth 18 and 32.

Expressed in more general terms, the axial movement A is thus converted into the rotary movement D for driving the counting ring 14 or gearwheel 15 by means of the first guide track 27 and/or the inclined plane 28 and an associated guide element 23 and/or a slide-like guide.

Preferably, the inclined plane 28 forms part of the first guide track 27. Particularly preferably, the inclined plane 28 is formed here by a helical track section. The helical track section in turn preferably forms part of the first guide track.

Particularly preferably, the nebuliser 1 or the counting device 12 or the drive device 16 thereof is configured such that even a partial actuation of the nebuliser 1, i.e. even a partial axial movement A, and in particular only the initial axial movement A, is sufficient for advancing the counting device 12, i.e. further rotating the counting ring 14 or gearwheel 15 by a numerical value. In the embodiment shown this is achieved by having the first guide track 27 or the inclined plane 28 designed such that adjoining the sloping section or the inclined plane 28 there is optionally an axially extending section 33 of the guide track 27. In this way it can be ensured that after the initial axial movement A, in the course of the continued axial movement A the drive element 17 and hence also the counting wheel 14 or gearwheel 15 are not rotated further. This ensures that only the initial axial movement A brings about the further rotation and hence advance of the counter. Accordingly, even if there is incomplete actuation of the nebuliser 1, particularly if the maximum stroke H is not achieved, counting can be continued correctly, as in this case, also, a dose of aerosol is usually delivered by the nebuliser 1.

In the embodiment shown, the slot or groove of the first guide track 27 initially runs at an inclination and then axially, starting from a position of engagement of the guide element 23 shown in FIG. 4, with the nebuliser 1 not actuated.

It should be noted that in the proposed nebuliser 1 or the proposed counter 12, the drive element 17 is preferably initially movable only axially towards the counting ring 14 or gearwheel 15 and only afterwards is it rotatable together with the latter. As already stated, this is achieved by means of the first guide track 27 and/or inclined plane 28 and the associated guide element 23. However, here again, different design solutions and/or procedures are also possible.

After the actuation of the nebuliser 1 has ended the axial movement A takes place in the opposite direction. In particular, the guide elements 23 are moved axially away again from the counting ring 14 or gear wheel 15. This can be assisted by a spring (not shown). This also causes the drive element 17 to be moved axially away from the gearwheel 15, so that they are moved out of engagement. Moreover, the drive element 17 is then rotated back into its starting position in the course of the continued axial movement back of the guide elements 23. This is in turn carried out as a result of the corresponding travel of the first guide tracks 27 or inclined planes 28. The nebuliser 1 is then ready to be actuated again.

In the embodiment shown the drive device 16 preferably has two guide elements 23 and/or first guide tracks 27, particularly on opposite sides, i.e. on two slide-like or positive guides. However, only one such guide may be provided.

Particularly preferably, the counter 12 has a barrier or latching device 34 for preventing the counting ring 14 and/or gearwheel 15 from turning backwards and/or for stepwise latching of the counting ring 14 and/or gearwheel 15. The barrier or latching device 34 in the embodiment shown preferably has a latching arm 35 that is elastically biased against the teeth 32 and/or in the axial direction, which is in particular formed or held by the guide sleeve 32 and/or formed thereon and/or disposed in a peripheral recess 36 in the drive element 17 as shown in FIG. 3.

However, other design solutions are also possible here. In particular, radial engagement and/or locking in one direction of rotation may also be provided.

Particularly preferably, the latching arm 35 together with the saw teeth 32 forms a rotation limiter that allows the gearwheel 15 to rotate in only one direction of rotation, namely the direction D for counting onwards.

Particularly preferably, the counter 12 forms a construction unit that can be inserted as a single unit in the housing 5 during assembly of the nebuliser 1. This makes assembly considerably easier.

The proposed counter 12 may also be used in other inhalers or nebulisers 1.

LIST OF REFERENCE NUMERALS

1 nebuliser
2 fluid
3 container
4 aerosol
5 housing
6 valve
7 valve stem
8 nozzle
9 connecting member
10 mouthpiece
11 housing part
12 counter
13 window
14 counting ring
15 gearwheel
16 drive device
17 drive element
18 teeth (drive element)
19 lower part
20 upper part
21 viewing window
22 guide part
23 guide element
24 guide sleeve
25 opening
26 depression
27 first guide track
28 inclined plane
29 second guide track
30 axial groove
31 projection
32 teeth (gearwheel)
33 axial section
34 latching device
35 latching arm
36 recess
37 shoulder
A axial movement
D direction of rotation
H stroke
L longitudinal axis

The invention claimed is:

1. A nebulizer (1) for dispensing an aerosol (4), having a counter (12) for counting actuations of the nebulizer (1) and/or doses of aerosol dispensed, the counter (12) comprising:

a counting ring (14) of annular configuration located about a central axis of the counter (12), the counting ring (14) being in communication with an annular gear (15) located about the central axis, the annular gear (15) comprising a plurality of teeth disposed annularly about the central axis and having respective peaks and valleys located on an outer surface of the annular gear (15) and directed axially, parallel with the central axis;

a drive element (17) of annular configuration located about the central axis and of rigid construction, including: (i) a plurality of teeth (18) disposed annularly about the central axis and having respective peaks and valleys located on an outer surface of the drive element (17) and directed axially, parallel with the central axis, and toward the plurality of teeth of the annular gear (15) of the counting ring (14); and (ii) a guide track (27) having at least one of an inclined track section and a helical track section located in a side wall of the drive element (17); and a guide part (22) of annular configuration located about the central axis, disposed co-axially within the drive element (17), and including a guide element (23) extending outward from a sidewall of the guide part (22) and radially away from the central axis and into engagement with the guide track (27), wherein the guide part (22) is restricted such that the guide element (23) is free to move axially, parallel to the central axis, but not rotationally about the central axis, wherein an axial actuating force on the guide part (22), relative to the central axis, causes: (i) the guide part (22) to move axially and the guide element (23) to bear against the guide track (27) of the drive element (17) such that an axial movement (A) of the guide part (22) is converted into a rotary movement (D) of the drive element (17) about the central axis; and (ii) the plurality of teeth (18) of the drive element (17) to engage the plurality of teeth of the annular gear (15) to rotate the counting ring (14) about the central axis.

2. The nebulizer according to claim 1, wherein, on actuation of the nebulizer (1), the drive element (17) is moved axially towards the counting ring (14) by means of the guide track (27) and the guide element (23); and only after such axial movement of the drive element (17), the counting ring (14) is rotated.

3. The nebulizer according to claim 1, wherein the guide track (27) forms a slot or a groove through the side wall of the drive element (17) in which the guide element (23) engages in a slidable manner.

4. The nebulizer according to claim 3, wherein the slot or the groove extends initially on a gradient and then axially, starting from a position of engagement of the guide element (23), when the nebulizer (1) is not actuated.

5. The nebulizer according to claim 1, wherein the guide part (22) comprises a further, opposing, guide element (23) and the drive element (17) comprises a further, opposing guide track (27).

6. The nebulizer according to claim 1, wherein the plurality of teeth (18) of the drive element (17) are in the form of saw teeth.

7. The nebulizer according to claim 1, wherein the plurality of teeth of the annular gear (15) in communication with the counting ring (14) are in the form of saw teeth.

8. The nebulizer according to claim 1, characterized in that the counter (12) comprises a barrier or latching device (34) to prevent the counting ring (14) from turning backwards and/or for the stepwise latching of the counting ring (14).

9. The nebulizer according to claim 1, wherein the counter (12) comprises a rotation limiter for limiting the rotation of the drive element (17).

10. The nebulizer according to claim 1, wherein the counter (12) comprises a guide sleeve (24) of annular configuration about the central axis and within which the drive element (17) is co-axially disposed, wherein the guide sleeve (24) is not rotatable about the central axis.

11. The nebulizer according to claim 10, wherein the guide sleeve (24) forms at least one of: (i) a barrier and/or latching device (34) to prevent the counting ring (14) from turning backwards; and (ii) a rotation limiter for limiting the rotation of the drive element (17), by at least one of radial engagement in a circumferential opening (36) in the drive element (17) and axial engagement in teeth (32) of the counting ring (14).

12. The nebulizer according to claim 10, wherein the guide sleeve (24) guides the guide element (23) in an axially movable manner, but secures it against rotation.

13. The nebulizer according to claim 1, wherein, on actuation of the nebulizer (1), a part of the nebulizer (1) performs a stroke (H) wherein the stroke (H) produces the actuating force on the guide part (22).

14. The nebulizer according to claim 13, characterized in that the guide track (27) is designed such that there is an axially extending section (33) of the guide track (27), so that axial movement caused by a partial actuation of the nebulizer, and a resultant partial stroke (H), is sufficient to advance the counting ring (14).

15. The nebulizer according to claim 1, wherein the nebulizer (1) is constructed as an inhaler for medicinal aerosol therapy.

16. The nebulizer according to claim 1, wherein the guide element (23) is axially guided by means of a further guide track (29) of the drive element (17).

* * * * *